US010813615B2

(12) United States Patent
Bracken et al.

(10) Patent No.: US 10,813,615 B2
(45) Date of Patent: Oct. 27, 2020

(54) MEDICAL VIEWING SYSTEM WITH A VIEWING ANGLE OPTIMIZATION FUNCTION

(71) Applicant: KONINKLIJKE PHILIPS N.V., Eindhoven (NL)

(72) Inventors: John Allan Bracken, Denver, CO (US); Niels Nijhof, Best (NL); Michael Grass, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1191 days.

(21) Appl. No.: 15/038,677

(22) PCT Filed: Nov. 5, 2014

(86) PCT No.: PCT/EP2014/073769
§ 371 (c)(1),
(2) Date: May 23, 2016

(87) PCT Pub. No.: WO2015/074869
PCT Pub. Date: May 28, 2015

(65) Prior Publication Data
US 2016/0302754 A1    Oct. 20, 2016

(30) Foreign Application Priority Data

Nov. 25, 2013  (EP) .................................... 13194184

(51) Int. Cl.
*A61B 6/00* (2006.01)
*A61B 8/12* (2006.01)
(Continued)

(52) U.S. Cl.
CPC .............. *A61B 6/5247* (2013.01); *A61B 6/12* (2013.01); *A61B 6/463* (2013.01); *A61B 6/467* (2013.01);
(Continued)

(58) Field of Classification Search
CPC ....... A61B 6/5247; A61B 34/25; A61B 90/37; A61B 6/503; A61B 8/467; A61B 8/463;
(Continued)

(56) References Cited

U.S. PATENT DOCUMENTS 8,942,457 B2 *  1/2015  Florent ................. G06T 11/008
                                                  128/922
10,238,361 B2 *  3/2019  Gogin ...................... A61B 6/00
(Continued)

FOREIGN PATENT DOCUMENTS

JP         2004329729 A    11/2004

OTHER PUBLICATIONS

Matthias, John et al "System to Guide Transcatherter Aortic Valve Implantations based on Interventional C-Arm CT Imaging", Medical Image Computing and Computer-Assisted Intervention MICCAI 2010.
(Continued)

*Primary Examiner* — Amanda Lauritzen Moher (57) ABSTRACT

An medical viewing system (10) adapted for acquiring a first set of X-ray fluoroscopy images of an ultrasonic probe (40) of an echocardiography imaging device at two different viewing angles, wherein a processing unit (30) of the system is adapted for registering live echocardiography and live X-ray images based on the first set of X-ray fluoroscopy images, localizing cusp nadirs positions of a set of characteristic features (42, 44, 46) in the X-ray subsequent frames, establishing a set of markers to match the localized positions of the cusp nadirs characteristic features (42, 44, 46), and determining an optimal viewing angle of the X-ray image acquisition device (12), in which the markers of the second set of markers lie on a single line and are equidistant from
(Continued)

each other in the X-ray field of view. This enables a precise alignment of the X-ray imaging device, especially for TAVR procedures.

20 Claims, 5 Drawing Sheets

(51) Int. Cl.
| | | |
|---|---|---|
| *G06T 7/00* | (2017.01) | |
| *A61B 6/12* | (2006.01) | |
| *A61B 8/08* | (2006.01) | |
| *A61B 90/00* | (2016.01) | |
| *A61B 34/00* | (2016.01) | |
| *A61B 8/00* | (2006.01) | |
| *A61B 17/00* | (2006.01) | |
| *A61B 8/14* | (2006.01) | |

(52) U.S. Cl.
CPC ............. *A61B 6/487* (2013.01); *A61B 6/503* (2013.01); *A61B 8/0883* (2013.01); *A61B 8/12* (2013.01); *A61B 8/463* (2013.01); *A61B 8/467* (2013.01); *A61B 8/5261* (2013.01); *A61B 34/25* (2016.02); *A61B 90/37* (2016.02); *G06T 7/0012* (2013.01); *A61B 6/4441* (2013.01); *A61B 8/14* (2013.01); *A61B 2017/00783* (2013.01); *A61B 2090/364* (2016.02); *A61B 2090/376* (2016.02); *A61B 2090/378* (2016.02); *A61B 2090/3784* (2016.02)

(58) Field of Classification Search
CPC ....... A61B 6/467; A61B 6/463; A61B 8/5261; A61B 8/0883; A61B 6/487; A61B 6/12; A61B 8/12; A61B 2090/378; A61B 2090/376; A61B 2090/3784; A61B 2090/364; A61B 8/14; A61B 2017/00783; A61B 6/4441; G06T 7/0012
See application file for complete search history.

(56) References Cited

U.S. PATENT DOCUMENTS

| | | | | |
|---|---|---|---|---|
| 10,282,638 | B2* | 5/2019 | Sun | G06K 9/6267 |
| 10,402,990 | B2* | 9/2019 | Popovic | A61B 5/04012 |
| 10,405,817 | B2* | 9/2019 | Wakai | A61B 6/54 |
| 2007/0021668 | A1* | 1/2007 | Boese | A61B 6/12 600/424 |
| 2007/0276243 | A1* | 11/2007 | Gerard | A61B 6/12 600/440 |
| 2011/0222750 | A1* | 9/2011 | Liao | A61B 6/4441 382/131 |
| 2013/0023766 | A1 | 1/2013 | Han | |
| 2013/0279780 | A1* | 10/2013 | Grbic | A61B 5/0033 382/131 |
| 2015/0223773 | A1* | 8/2015 | John | A61B 8/0841 600/424 |
| 2017/0079600 | A1* | 3/2017 | Bracken | A61B 6/12 |
| 2018/0130200 | A1* | 5/2018 | Miao | G06T 7/74 |

OTHER PUBLICATIONS

Gao, Gang et al "Registration of 3D trans-esophageal echocardiography to X-ray fluoroscopy using image-based probe tracking", Medical Image Analysis, vol. 16, No. 1, May 2011.
Mountney, Peter et al "Ultrasound and Fluoroscopic Images Fusion by Autonomous Ultrasound Probe Detection", Medical Image Computing and Computer-Assisted Intervention MICCAI 2012.
"Valve Planning Protocol—Visualization and Quantification of Cardiac Anatomy for Effecive Treatment Strategies", 2012.
Jain, Ameet et al "3D TEE Registration with X-Ray Fluoroscopy for Interventional Cardiac Applications", Functional Imaging and Modeling of the Heart, 2009, pp. 321-329.
Zheng, Yefeng et al "Automatic Aorta Segmentation and Valve Landmark Detection in C-Arm CT: Application to Aortic Valve Implantation", Medical Image Computing and Computer-Assisted Intervention MICCAI 2010.
Goshtasby, A.A. "Image Registration Principles, Tools and Methods", 2012.

* cited by examiner

MEDICAL VIEWING SYSTEM WITH A VIEWING ANGLE OPTIMIZATION FUNCTION

CROSS-REFERENCE TO PRIOR APPLICATIONS

This application is the U.S. National Phase application under 35 U.S.C. § 371 of International Application No. PCT/EP2014/073769, filed on Nov. 5, 2014, which claims the benefit of European Patent Application No. 13194184.1, filed on Nov. 25, 2013. These applications are hereby incorporated by reference herein.

FIELD OF THE INVENTION

The invention relates to a medical viewing system, a method for providing medical images, a computer program element and a computer readable medium.

BACKGROUND OF THE INVENTION

Two-dimensional X-ray imaging is a dominant imaging modality for cardiac interventions. For providing a guidance of procedures that require soft-tissue information, for example, the treatment of structural heart disease, echocardiography information are also employed. For example, transcatheter aortic valve replacement procedures (TAVR) are challenging procedures in interventional cardiology that depend on both live X-ray (fluoroscopy) and live ultrasound (echocardiography) imaging. To deploy a prosthetic replacement of an aortic valve safely an optimal viewing angle for the position of an X-ray image acquisition device, e.g. a C-arm imaging device, is required. The optimal viewing angle for deploying a prosthetic valve is the X-ray viewing angle at which the bottoms (nadirs) of all three cusps of the native (or original) aortic valve are visible in the X-ray images. The cusp nadirs should line up with each other and be equally spaced apart in the X-ray images at the optimal viewing angle.

Image guidance systems exist that have a potential to aid cardiologists in quickly finding an optimal C-arm viewing angle during a TAVR procedure by fusing live X-ray images and live echocardiography (transesophageal echocardiography, TEE) images together. Markers manually placed on TEE images of the valve cusps will automatically display at the approximate cusp positions on the X-ray images.

SUMMARY OF THE INVENTION

However, the alignment of the markers to the cusp nadirs in the X-ray images, if this approach is used, may be subject to an improvement. The nadirs are difficult to locate in the above mentioned TEE images.

Consequently, it is an object of the invention to provide an imaging system, which is able to fuse live fluoroscopy images and echocardiography images together, while the alignment of the markers to the cusp nadirs in the X-ray images is improved, such that the system is useful for locating the optimal viewing angle for valve deployment.

The object is met by a system having the features of independent claim 1. Advantageous embodiments and further improvements may be gathered from the subclaims and the following description.

A medical viewing system is proposed, comprising an X-ray image acquisition device for providing live X-ray images from a variable viewing angle, an echocardiography imaging device having an ultrasonic probe for providing live ultrasound images, and a processing unit connectable to the X-ray image acquisition device and the echocardiography imaging device. The medical viewing system is adapted for acquiring a first set of X-ray fluoroscopy images of the ultrasonic probe at two different viewing angles. The processing unit is adapted for registering live ultrasound and live X-ray images based on the first set of X-ray fluoroscopy images, localizing positions of a set of characteristic features in subsequent frames, establishing a set of markers to match the recognized positions of the characteristic features, and determining an optimal viewing angle of the X-ray image acquisition device, in which the markers comprise a predetermined relationship in the X-ray field of view.

The X-ray image acquisition device may preferably comprise a C-arm assembly, which includes a C-arm structure with an X-ray source and an X-ray detector mounted across from the X-ray source and a motorized drive for a rotational movement of the C-arm structure. The C-arm structure is provided to perform a rotational scan around an axis of rotation and around an ISO-centre acquiring a number of X-ray projections at variable viewing angles. The processing unit, which is connected to the X-ray image acquisition device, is capable of controlling the motion of the C-arm structure and the acquisition of X-ray images.

The echocardiography imaging device is to be understood as an imaging device having a probe containing an ultrasound transducer at its tip, which probe may be passed into or placed onto the patient's body, for providing live ultrasound images and Doppler evaluation. The probe may be chosen from a variety of different probes, such as a transesophageal echocardiography (TEE) probe, which is to be inserted into the patient's esophagus, or a transthoracic echocardiography (TTE) probe, which is to be placed onto the patient's thorax. In particular, TEE provides cardiologists with real-time three-dimensional imaging of cardiac anatomy.

The processing unit is to be understood as a computing unit having a processor, a memory and an interface for receiving user inputs and live image data from the X-ray image acquisition device and the echocardiography imaging device and for outputting data and control signals. Further, the processing unit is adapted for executing a number of algorithms for performing the above mentioned functions.

A basic, preparational function for enabling a reasonable fusion of X-ray image data and echocardiography data lies in providing the first set of X-ray fluoroscopy images of the echocardiography probe at two different viewing angles. This allows one to conduct an image-based echocardiography probe localization without the necessity to employ further tracking devices.

After conducting the probe localization, a precise real time registration of three-dimensional echocardiography images and two-dimensional fluoroscopy images is possible. This may be conducted through any of well-known registration techniques, which shall not limit the scope of protection.

The processing unit is furthermore capable of localizing the positions of a set of characteristic features of the body/organ to be examined, such as cusp nadirs of an aortic valve. This may be accomplished through different processes, which may be automatic or semi-automatic. For example, the processing unit is adapted for receiving a preliminary set of marker positions, which may be input by an interventionist or may be estimated by the processing unit. This preliminary set of marker positions may in particular be prepared in the three-dimensional echocardiography images. However, they may also be set in the live two-dimensional X-ray images. As an alternative to this, also three-dimensional image data may be used from one of the image modalities to establish the set of markers.

Once the coordinates of the positions of the set of characteristic features have been localized, the coordinates of these positions are automatically assigned to the marker positions. This assignment may be straightforward, for example with the non-coronary cusp and left coronary cusp located in the lower left region and upper right regions of the search area of the aortogram images, respectively. Simultaneously, the marker positions would be automatically adjusted on the echocardiography images as well, since the live echocardiography images are sent to the processing unit at the same time as the live aortogram images and are also registered with them.

Once the markers are placed at the localized positions, the processing unit is easily able to adjust the viewing angle of the X-ray image acquisition device. This means, that the X-ray image acquisition device is controlled to quickly rotate to the optimal viewing angle, where the (set of) markers comprises the predetermined relationship. In particular, for a TAVR procedure, they lie on a single line and are equidistant from each other in the X-ray field of view. For other procedures, other relationships may be possible.

The medical viewing system therefore provides a precise positioning of the X-ray viewing device to an optimal viewing angle, since the markers are located on the cusp nadirs. This technique clearly simplifies and improves clinical workflow in particular for TAVR procedures when using this medical viewing system to determine the optimal viewing angle.

It is to be understood that without any prior indication of what the optimal viewing angle is before the procedure starts, multiple aortograms would be required to determine this angle. For example, by placing markers on the cusps in live echocardiography images, with an automatic correction to align the markers to the valve cusp nadirs in an aortogram would require only a single aortogram to find the optimal viewing angle instead of several of them.

Therefore, the imaging system according to the invention has a large potential to reduce both radiation dose and contrast agent use to the patient until the ideal angle has been found.

The method, which is achievable through this medical viewing system, may also be applied for the replacement of any other heart valve, e.g. the mitral valve.

It is preferred that the medical viewing system is also adapted for moving the X-ray image acquisition device to the determined optimum viewing angle.

In an advantageous embodiment, localizing the positions of the set of characteristic features comprises recognizing the positions of the set of characteristic features in echocardiography images or X-ray images, i.e. the aortogram, around a preliminary set of markers given by an operator, wherein the processing unit is further adapted for adjusting the preliminary set of markers according to the recognized positions.

To improve the precision of the markers positions of this preliminary set of markers, exemplarily an X-ray aortogram at a fixed viewing angle is acquired. In this context, an aortogram in particular comprises a sequence of images taken by the X-ray image acquisition device of the heart valves. For providing a sufficient opacity and a better improved visual detectability of the heart valves and their surroundings, these images are acquired after a contrast agent (CA) is injected into a vessel or heart chamber. It goes without saying, that the aortogram may also comprise only one image under an injected contrast agent. Also, instead of the expression "aortogram" also the expression "valvogram" may be suitable for describing this process.

The aortogram images allow one to conduct an automated search in particular for the valve cusp nadirs in the aortogram image sequence. The point or feature detection search algorithm may attempt to locate the cusp nadirs in subsequent frames of the aortogram image sequence as they are being received and displayed through the processing unit. Since the nadirs are the locations on the valve cusps where the cusp curvature changes direction, this may simplify the search.

The medical viewing system therefore provides a precise correction by performing a point or feature detection search on one or several image frames of the live or saved aortogram image sequence to locate in particular the nadirs of the native aortic valve cusps. The markers will then be automatically moved and aligned to the valve cusp nadirs in the aortogram. Since the live X-ray and live echocardiography images are transferred to and registered in the processing unit at the same time, the marker positions will also be automatically corrected and updated in the echocardiography images after being updated in the aortogram.

In other words, the medical viewing system according to the invention provides a correction technique, which makes use of the information contained in an X-ray aortogram image sequence, which has already been obtained as a part of a standard of care before prosthetic valve positioning and deployment. The valve cusp nadirs can be detected more easily in the aortogram than in the echocardiography images. This technique uses an algorithm to automatically move the markers to the valve cusp nadirs based on the feature information in the aortogram image sequence.

In a further exemplary embodiment, the processing unit is adapted for recognizing the positions of the set of characteristic features in a central region of the X-ray image sequence. The processing unit may be adapted for recognizing cusp nadirs in a central region of the X-ray image sequence and in particular of a region centered around a marker position of a right coronary cusp on a first frame of the X-ray image sequence. The required effort for the algorithm to recognize the markers can thereby be clearly reduced.

In a still further embodiment, the processing unit is adapted for constantly tracking the motion of the set of markers based on the echocardiography images. For example, after the set of markers has been established, it is clearly advantageous to ensure that the markers remain on the nadirs as the aortic root moves. Furthermore the viewing angle of the X-ray image acquisition device may repeatedly readjusted. Both imaging modalities may be used to track the marker positions, but this will likely be simpler to conduct based on the echocardiography images, since marker motion tracking would not be possible when there is no longer any contrast agent in the X-ray images to show the locations in particular of the cusp nadirs.

In a further advantageous embodiment, the processing unit is adapted for extracting positions of the set of characteristic features from a three-dimensional model of at least one organ of interest, e.g. the aortic valve, for forming the set of markers. In particular, this embodiment would overcome the necessity of having to manually place markers on the echocardiography or aortogram images of the aortic valve cusps, since the cusp nadir locations are already known in the model and these nadir locations in the model may easily be adapted to the nadir positions in the aortogram image sequence. Since the model mesh just needs to be conformed and adapted to the aortogram image sequence of the aortic valve and the cusp nadirs locations are already known in the model, this embodiment will also remove the need to search for the cusp nadirs in the aortogram.

In another embodiment the processing unit may be adapted for generating such a three-dimensional model as a preparational process for the intervention. In particular, this model may be created from multiple previously acquired CT image data sets of the aortic valve. The model may have the location of the characteristic features pre-marked, and the model could then be automatically adapted to fit the native organ in saved or live aortogram images as they are received by the processing unit.

In a still further embodiment, the processing unit may be adapted for recording, saving and replaying the aortogram run. This may be helpful as an additional option to facilitate the placement of the first set of markers on the positions of the characteristic features. For example, the automatic search algorithm to detect the nadirs could be attempted on either the entire saved image sequence of the aortogram or on a single image frame of the aortogram. For the case of using a single image frame, the user would have the option to select which image frame to use to locate the cusp nadirs. The option of being able to manually place markers on the cusp nadirs in either the entire saved aortogram image sequence or on a single image frame would be very helpful if the automated search for the nadirs does not succeed. Once the markers have been moved to the nadirs using either the automatic or manual approach on the saved aortogram images, the marker positions will be recorded and updated on the live TEE images.

The invention also relates to a method for providing medical images, comprising the steps of acquiring a first set of X-ray fluoroscopy images of an ultrasonic probe of an echocardiography imaging device at two different viewing angles by means of an X-ray image acquisition device, registering live echocardiography and live X-ray images based on the first set of X-ray fluoroscopy images by means of a processing unit, localizing the positions of the set of characteristic features in the X-ray subsequent frames, establishing a set of markers to match the localized positions and determining an optimal viewing angle of the X-ray image acquisition device, in which the markers of the set of markers comprise a predetermined relationship in the X-ray field of view, e.g. lie on a single line and are equidistant to each other for a TAVR procedure. It is advantageous to also control the X-ray image acquisition device to move to the determined optimum viewing angle. These and the following method steps are in analogy to the above description of the medical viewing system.

In an advantageous embodiment, the method further comprises the steps of recognizing positions of the characteristic features in echocardiography images or X-ray images around a preliminary set of markers given by an operator, and adjusting the preliminary set of markers according to the recognized positions.

Further, recognizing these positions may be conducted in a central region of the X-ray image sequence, in particular of a region centered around a marker position of a right coronary cusp on a first frame of the X-ray image sequence.

In an alternative embodiment, the method comprises extracting positions of the set of characteristic features from a three-dimensional model of at least one organ of interest for forming the set of markers.

Also, the method may also comprise the step of automatically fitting the native organ in saved or live aortogram images as they are received by the processing unit.

It goes without saying, that the set of characteristic features may comprise valve cusp nadirs and other characteristic features of certain organs of a body, in particular a human body.

These and other aspects of the present invention will become apparent from and be elucidated with reference to the embodiments described hereinafter.

DETAILED DESCRIPTION OF EMBODIMENTS

Figure 1:
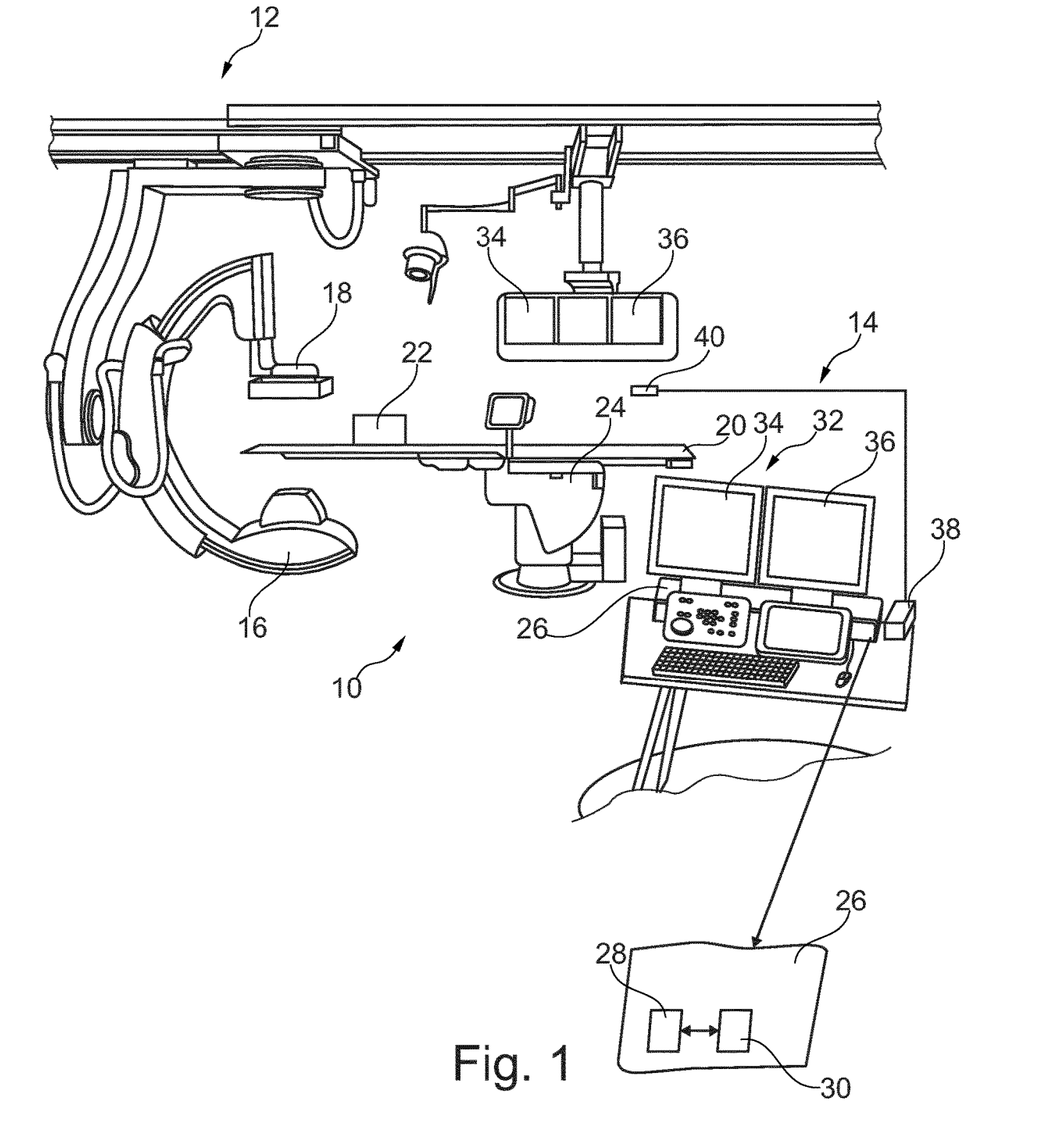
FIG. 1 shows a medical viewing system in a schematic view.

According to the example of FIG. 1, a medical viewing system 10 is provided, comprising an X-ray image acquisition device 12, and a medical image viewing device 14. The X-ray image acquisition device 12 comprises an X-ray source 16 and an X-ray detector 18. The X-ray image acquisition device 12 is configured to provide X-ray images of an object. Further, a support table 20, for example for receiving an object, such as a patient, is shown, who may receive a contrast agent from a contrast agent injector 22 for introducing a contrast agent into vessels of a patient. A control unit 24 may be present to control the X-ray image acquisition device 12.

It should be noted that the X-ray image acquisition device 12 shown in FIG. 1 is shown as a C-arm structure. However, also other X-ray image acquisition devices, movable or non-movable, may be used without departing from the concept of the invention.

The medical image viewing device 14 exemplarily comprises a calculation unit 26, which inter alia includes an image data providing unit 28 and a processing unit 30. The medical image viewing device 14 also comprises a display unit 32 with a first display 34 and a second display 36, which may also be found at the X-ray image acquisition device 12.

The image data providing unit 28 is exemplarily configured to provide aortographic images of a region of interest of an object.

Also, an echocardiography imaging device 38 having an ultrasonic probe 40 is present, which may be a TEE probe, for acquiring echocardiographic images, which are provided to the processing unit 30 as well.

The processing unit 30 is connectable to the X-ray image acquisition device 12 and the echocardiography imaging device 38 and is adapted for registering live echocardiography and live X-ray images based on the first set of X-ray fluoroscopy images, localizing cusp nadirs in the X-ray subsequent frames, establishing a set of markers to match the localized positions of the cusp nadirs, and determining an optimal viewing angle of the X-ray imaging device, in which the markers of the set of markers lie on a single line and are equidistant from each other in the X-ray field of view. The X-ray image acquisition device 12 is controllable to move to this optimal viewing angle.

The display unit 32 is configured to display X-ray images and echocardiography images on their own and as a fusion. The data connection between all components may be provided by wire connection and by wireless connection. Further, the processing unit 30 and the image data providing unit 28 may also be separate devices, not included in a single calculation unit.

In an example, not further shown, the processing unit 30 localizes cusp nadir positions in echocardiography images or X-ray images around a preliminary set of markers given by an operator, wherein the processing unit is further adapted to adjust the preliminary set of markers according to the recognized cusp nadir positions. The recognition may take place in a particular region centered around a marker position of a right coronary cusp on a first frame of an X-ray image sequence.

However, the processing unit 30 may also create or receive a three-dimensional model of an aortic valve and for extracting positions of valve cusp nadirs from this model.

The processing unit 30 may automatically fit the native aortic valve in saved or live aortogram images as they are received by the processing unit 30.

Figure 2:
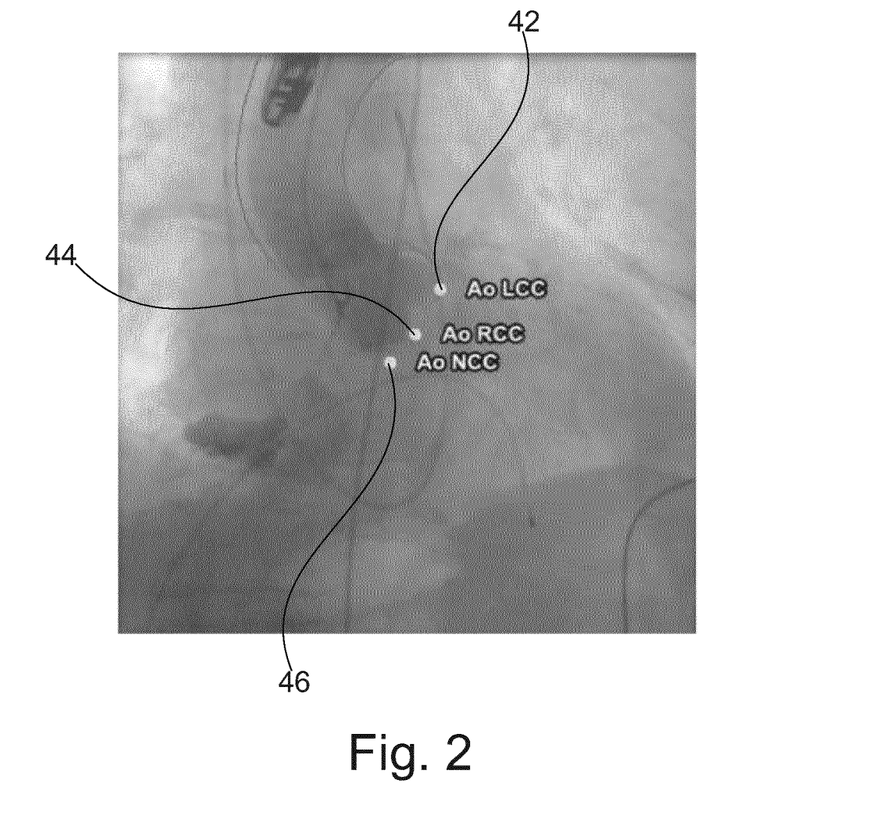
FIG. 2 shows an aortogram with valve cusp nadirs.

In FIG. 2, the requirements for an optimal viewing angle of a C-arm X-ray image acquisition device 12 are shown. For example, in a transcatheter aortic valve replacement (TAVR) interventional process, a diseased native aortic valve is replaced with a prosthetic valve, which is delivered with a catheter and guidewire and deployed in the aortic root. This procedure is carried out using both live X-ray (fluoroscopy and aortography) and live transesophageal echocardiography (TEE) image guidance. The optimal viewing angle of the x-ray C-arm system for TAVR procedures should show the three nadirs (bottoms) of the aortic valve cusps approximately aligned with each other and equidistant from each other. The three cusps, left coronary cusp (LCC) 42, right coronary cusp (RCC) 44 and non-coronary cusp (NCC) 46 are shown in this X-ray aortogram image of FIG. 2.

Figure 3:
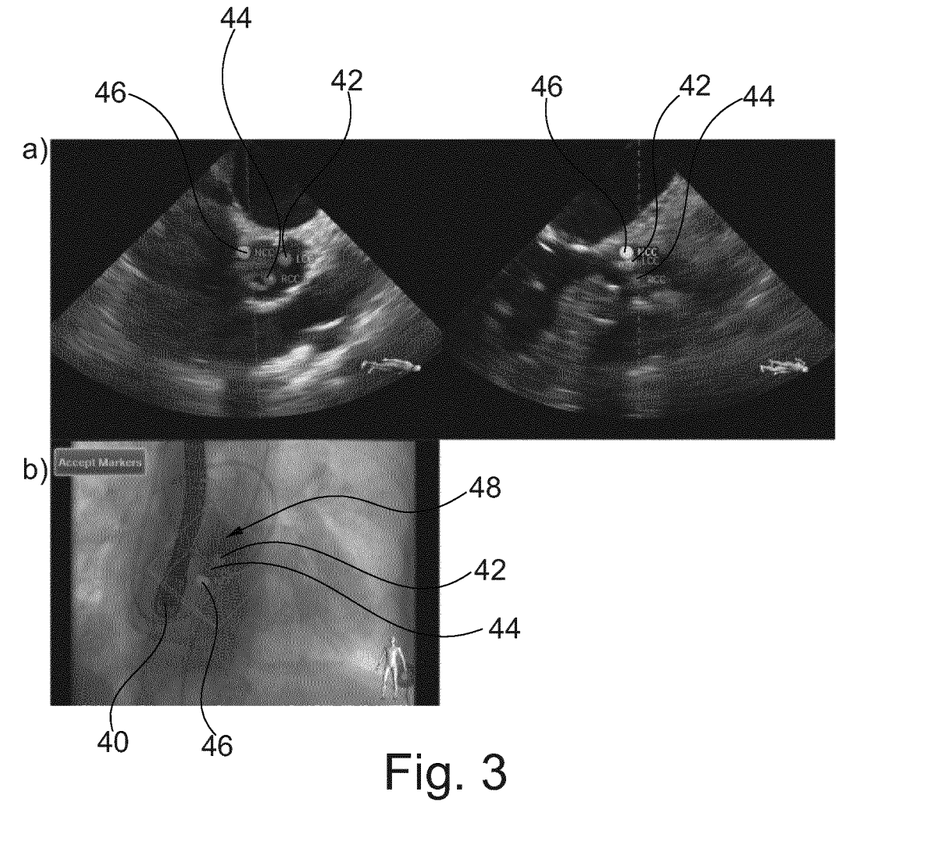
FIG. 3 shows a process for adjusting a preliminary set of markers by means of echocardiography and X-ray images.

In FIG. 3, the process of adjusting a preliminary set of markers for marking the three cusp nadirs 42, 44 and 46 is shown. In the upper section a) preliminary markers for the left coronary cusp (LCC) 42, the right coronary cusp (RCC) 44 and the non-coronary cusp (NCC) 46 are placed on orthogonal 2D views of the aortic valve cusps in 2D x-plane echocardiography images. As visible in the lower section b) the preliminary set of markers of the valve cusp nadirs do not align well with the valve cusp nadirs in an X-ray aortogram image. An aorta lumen 48 is visible with the assistance of contrast agent being injected into the patient. The probe 40 used to generate the echocardiography images is also visible in the aortogram.

Figure 4:
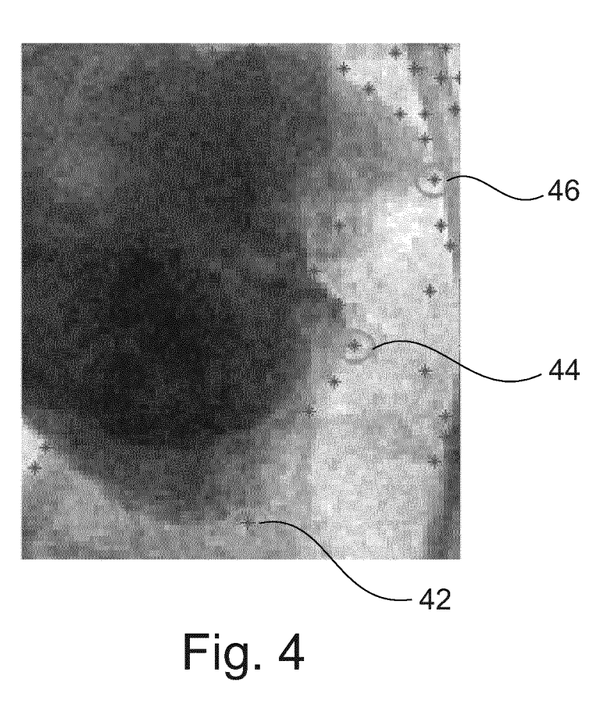
FIG. 4 shows an example of an automatic feature detection on an X-ray aortogram.

However, in FIG. 4 an example of an automatic feature detection search on an X-ray aortogram frame to locate the cusp nadirs 42, 44 and 46 is shown. The nadirs are shown within circles. The detection of other features may be excluded through adequate filters and a smaller search window.

Figure 5:
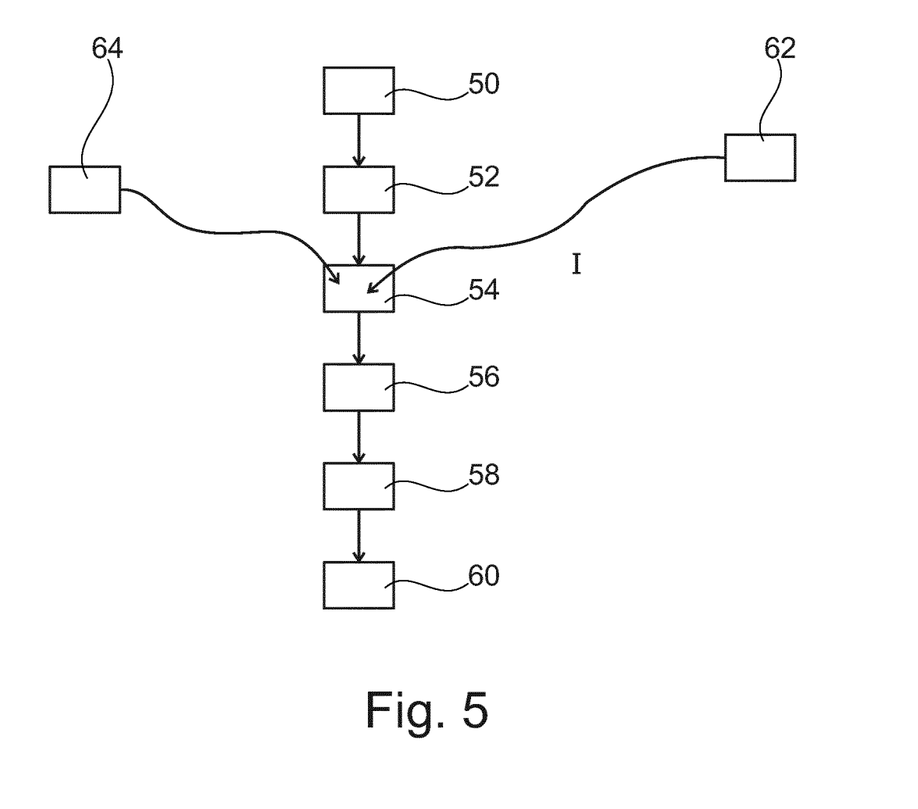
FIG. 5 demonstrates the method according to the invention in a schematic, block-oriented view.

In FIG. 5, the method according to the invention is shown in a block-oriented, schematic view. Basically, the method comprises the steps of acquiring 50 a first set of X-ray fluoroscopy images of an ultrasonic probe 40 of an echocardiography imaging device 38 at two different viewing angles by means of an X-ray image acquisition device 12, registering 52 live echocardiography and live X-ray images based on the first set of X-ray fluoroscopy images by means of a processing unit 30, localizing 54 cusp nadirs in the X-ray subsequent frames, establishing 56 a set of markers to match the localized positions of the cusp nadirs, determining 58 an optimal viewing angle of the X-ray image acquisition device 12, in which the markers of the set of markers lie on a single line and are equidistant from each other in the X-ray field of view, and controlling 60 the X-ray image acquisition device 12 to move to the determined optimum viewing angle.

However, localizing 54 may be conducted through recognizing 62 cusp nadir positions in echocardiography images or X-ray images around a preliminary set of markers given by an operator, such that establishing the set of markers is conducted through adjusting the preliminary set of markers according to the recognized cusp nadir positions. This option is marked with "I". Still further, recognizing 62 cusp nadir positions may be conducted in a central region of the X-ray image sequence, in particular of a region centered around a marker position of a right coronary cusp on a first frame of the X-ray image sequence.

In an alternative embodiment, which is marked with "II", localizing 54 may be conducted through extracting 64 positions of valve cusp nadirs 42, 44, 46 from a three-dimensional model of the aortic valves for forming the set of markers.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

LIST OF REFERENCE SIGNS

10 Medical viewing system
12 X-ray imaging system
14 Medical image viewing device
16 X-ray source
18 X-ray detector
20 Support table
22 Contrast agent injector
24 Control unit
26 Calculation unit
28 Image data providing unit
30 Processing unit
32 Display unit
34 First display
36 Second display
38 Echocardiography imaging device
40 Ultrasonic probe
42 Left coronary cusp (LCC)
44 Right coronary cusp (RCC)
46 Non-coronary cusp (NCC)
48 Aorta lumen
50 Acquiring a first set of X-ray fluoroscopy images
52 Registering live echocardiography and X-ray images
54 Localizing positions of a set of characteristic features
56 Establishing a set of markers
58 Determining an optimal viewing angle
60 Controlling X-ray imaging device
62 Recognizing positions of characteristic features
64 Extracting positions of set of characteristic features

The invention claimed is:

1. A system, comprising:
   an X-ray image acquisition device having a field of view and a controllable viewing angle;
   an echocardiography imaging device including an ultrasonic probe; and
   a processing unit, wherein the processing unit is connected to the X-ray image acquisition device to receive live X-ray images from the X-ray image acquisition device and to control an orientation of the X-ray image acquisition device, and wherein the processing unit is connected to the echocardiography image acquisition device to receive live echocardiography images from the echocardiography image acquisition device, and
   wherein the processing unit:
      controls a position of the X-ray image acquisition device to acquire a first set of X-ray fluoroscopy images of the ultrasonic probe at two different viewing angles,
      registers the live echocardiography images and the live X-ray images to each other based on the first set of X-ray fluoroscopy images,
      localizes positions of a set of aortic valve cusp nadirs in the live X-ray images acquired by the X-ray image acquisition device subsequent to the registration,
      establishes a set of markers to match the localized positions of the set of aortic valve cusp nadirs in the live X-ray images acquired by the X-ray image acquisition device subsequent to the registration, and
      determines an optimal viewing angle of the X-ray image acquisition device, in which the markers of the set of markers which are matched to the localized positions of the set of aortic valve cusp nadirs appear spaced equally apart in a single straight line in the field of view of the X-ray image acquisition device.

2. The system of claim 1, wherein the X-ray image acquisition device comprises a C-arm X-ray image acquisition device which is movable to change its viewing angle.

3. The system of claim 1, further comprising a display unit for displaying the live X-ray images and the live echocardiography images individually, and fused together.

4. The system of claim 1, wherein localizing positions of the set of aortic valve cusp nadirs comprises recognizing the positions of the set of aortic valve cusp nadirs in the live echocardiography images or the live X-ray images around a preliminary set of markers given by an operator,
   wherein the processing unit is further adapted to adjust the preliminary set of markers according to the recognized positions.

5. The system of claim 1, wherein the processing unit extracts positions of the set of characteristic features for forming the set of markers from a three-dimensional model of at least the aortic valve.

6. A system, comprising:
   an X-ray image acquisition device for providing live X-ray images from a variable viewing angle, wherein the X-ray image acquisition device has a field of view,
   an echocardiography imaging device having an ultrasonic probe for providing live echocardiography images, and
   a processing unit connected to the X-ray image acquisition device and the echocardiography imaging device,
   wherein the X-ray image acquisition device and processing unit acquire a first set of X-ray fluoroscopy images of the ultrasonic probe at two different viewing angles,
   wherein the processing unit:
      registers the live echocardiography images and the live X-ray images to each other based on the first set of X-ray fluoroscopy images,
      localizes positions of a set of characteristic features in the live X-ray images acquired by the X-ray image acquisition device, establishes a set of markers to match the localized positions of the characteristic features in the live X-ray images acquired by the X-ray image acquisition device, and determines an optimal viewing angle of the X-ray image acquisition device, in which the markers of the set of markers comprise a predetermined relationship in the field of view of the X-ray image acquisition device.

7. The system of claim 6,
wherein the set of characteristic features comprises cusp nadirs.

8. The system of claim 6, wherein the X-ray image acquisition device comprises a C-arm X-ray image acquisition device which is movable to change its viewing angle.

9. The system of claim 6, further comprising a display unit for displaying the live X-ray images and the live echocardiography images individually, and fused together.

10. A method, comprising:
acquiring a first set of X-ray fluoroscopy images of an ultrasonic probe of an echocardiography imaging device at two different viewing angles, by an X-ray image acquisition device having a field of view, registering live echocardiography images acquired by the ultrasonic probe and live X-ray images acquired by the X-ray image acquisition device to each other based on the first set of X-ray fluoroscopy images, by a processing unit, localizing positions of a set of characteristic features in the live X-ray images acquired by the X-ray image acquisition device, establishing a set of markers to match the localized positions of the characteristic features in the live X-ray images acquired by the X-ray image acquisition device, and determining an optimal viewing angle of the X-ray image acquisition device, in which the markers of the set of markers comprise a predetermined relationship in the field of view of the X-ray image acquisition device.

11. The system of claim 6,
wherein localizing positions of the set of characteristic features comprises recognizing the positions of the set of characteristic features in the live echocardiography images or the live X-ray images around a preliminary set of markers given by an operator, wherein the processing unit is further adapted to adjust the preliminary set of markers according to the recognized positions.

12. The system of claim 11,
wherein the processing unit recognizes the characteristic features in a central region of the live X-ray images.

13. The system of claim 6, wherein the processing unit extracts positions of the set of characteristic features for forming the set of markers from a three-dimensional model of at least one organ of interest.

14. The system of claim 13,
wherein the processing unit automatically fits the extracted positions of the set of characteristic features to a native organ in saved or live aortogram images as they are received by the processing unit.

15. The method of claim 10, further comprising displaying the live X-ray images and the live echocardiography images individually, and fused together.

16. The method of claim 10,
wherein localizing the positions of a set of characteristic features in the live X-ray images comprises localizing cusp nadirs.

17. The method of claim 10, further comprising
recognizing the positions of the set of characteristic features in the live echocardiography images or the live X-ray images around a preliminary set of markers given by an operator, and adjusting the preliminary set of markers according to the recognized positions.

18. The method of claim 10,
wherein recognizing the positions of the set of characteristic features is conducted in a central region of the live X-ray images.

19. The method of claim 8, further comprising:
extracting positions of the set of characteristic features for forming the set of markers from a three-dimensional model of an organ of interest.

20. The method of claim 19, further comprising:
automatically fitting the extracted positions of the set of characteristic features to a native organ in saved or live aortogram images as they are received by the processing unit.

* * * * *